(12) United States Patent
Bourland et al.

(10) Patent No.: US 9,615,807 B2
(45) Date of Patent: Apr. 11, 2017

(54) SYSTEMS AND METHODS FOR IMPROVING IMAGE QUALITY IN CONE BEAM COMPUTED TOMOGRAPHY

(71) Applicants: John Daniel Bourland, Winston-Salem, NC (US); Jie Liu, Winston-Salem, NC (US)

(72) Inventors: John Daniel Bourland, Winston-Salem, NC (US); Jie Liu, Winston-Salem, NC (US)

(*) Notice: Subject to any disclaimer, the term of this patent is extended or adjusted under 35 U.S.C. 154(b) by 29 days.

(21) Appl. No.: 14/262,657

(22) Filed: Apr. 25, 2014

(65) Prior Publication Data

US 2014/0321604 A1    Oct. 30, 2014

Related U.S. Application Data

(60) Provisional application No. 61/816,504, filed on Apr. 26, 2013.

(51) Int. Cl.
*A61B 6/03* (2006.01)
*A61B 6/00* (2006.01)
*G01N 23/04* (2006.01)
*G06T 11/00* (2006.01)

(52) U.S. Cl.
CPC .......... *A61B 6/5282* (2013.01); *A61B 6/4085* (2013.01); *A61B 6/5205* (2013.01); *G01N 23/046* (2013.01); *G06T 11/006* (2013.01); *A61B 6/032* (2013.01); *A61B 6/583* (2013.01); *G01N 2223/401* (2013.01); *G06T 2211/428* (2013.01)

(58) Field of Classification Search
CPC ....... A61B 6/5282; A61B 6/583; A61B 6/032; A61B 6/482; A61B 6/542; A61B 6/463; A61B 6/469; A61B 6/504; A61B 6/06; A61B 6/5217; A61B 6/4441; A61B 6/465; A61B 6/405; A61B 6/481; A61B 6/502; A61B 6/5205; A61B 6/4021; A61B 6/484; A61B 6/487; G01N 2223/401; G01N 23/046; G06T 11/006; G06T 2211/428
USPC .................................................. 378/4, 7, 62
See application file for complete search history.

(56) References Cited

U.S. PATENT DOCUMENTS

2013/0051516 A1* 2/2013 Yang ........................ A61B 6/03
378/4

* cited by examiner

*Primary Examiner* — Glen Kao
(74) *Attorney, Agent, or Firm* — Ben Schroeder Law, PLLC (57) ABSTRACT

The present invention focuses on an analytical model for fast and accurate scatter estimation. The present invention uses the Klein-Nishina (KN) formula as a starting point, which gives the Compton scattering differential cross-section for an interaction point. For a direct integration of the point scatter kernel over the irradiated volume, the large number of KN formulae (e.g., amount of solid angle subtended) and rays traced required for calculating attenuation makes the computation very expensive. The present invention reduces the 3D formulation into an efficient 2D approach by integrating the KN formula along an interaction line of tissue-equivalent medium. An average attenuation length was assumed for each interaction point on the beam to reduce the number of rays traced. In the case of kilovoltage (kV) x rays as the imaging source and a small imaging field, with in-field scatter, the line integral derived, can be approximated by a compact analytical form.

15 Claims, 10 Drawing Sheets

*integrated scatter at pixel P*:

$$N_\sigma(\vec{r}) = \int_{x^-}^{x^+} dN(x)\,dx \approx \left[f_0 - f_2 \cdot \|\vec{u}\|^2 + f_4 \cdot \|\vec{u}\|^4\right] + (\vec{r}\cdot\vec{n})\left[f_0' - f_2' \cdot \|\vec{u}\|^2 + f_4' \cdot \|\vec{u}\|^4\right]$$

where $\vec{u} = \vec{r} - (\vec{r}\cdot\vec{n})\vec{n}$ and $f_i, f_i'$ $(i = 0, 2, 4)$ are pencil beam dependent coefficients.

SYSTEMS AND METHODS FOR IMPROVING IMAGE QUALITY IN CONE BEAM COMPUTED TOMOGRAPHY

This application claims priority under 35 USC 119(e) to U.S. Provisional Application No. 61/816,504 filed Apr. 26, 2013, the entire contents of which are incorporated by reference in its entirety.

FIELD OF THE INVENTION

The present invention relates to computed tomography (CT) imaging systems and methods, in an embodiment, the invention relates to CT imaging systems and methods for probing internal structures of an object using x-ray ionizing radiation. In a variation, the present invention relates to x-ray ionizing radiation image recording methods and apparatuses for use in a cone-beam computed tomography (CBCT) systems.

BACKGROUND OF THE INVENTION

Scattered photons are produced in a subject being x-ray imaged either from x-ray Compton interactions (which is the dominant form) and x-ray Rayleigh interactions (the less dominant form). These scattered photons degrade CT and CBCT image quality by contributing a background fluence to image pixels that decreases the signal-to-noise-ratio (SNR). It is desirable to identify the scatter contributions in an image and thereby make it possible to remove the scatter from the acquired image to greatly improve image quality. X-ray scatter due to the Compton interaction is difficult to measure directly without disturbing the image itself. Instead of direct measurement of x-ray scatter a method can be used to calculate the scatter. First order Compton scatter interactions have been modeled by the Klein-Nishina (KN) formula. Direct implementation to calculate Compton scattered photons using the KN point model can be accomplished by dividing a volumetric object into (N) (N) (N) voxels. Thus, when performing a calculation using the KN model, the calculation expense for using the point model is $N^3 \times M^2$ calculations (wherein M is a dimension in two dimensional space of the three dimensional object projected/reduced into two dimensions). It would thus be desirable to be able to reduce the number of calculations needed to identify scatter contributions, and to do so faithfully without greatly diminishing the image quality, and in fact to enable the improvement in image quality by removal of calculated scatter from the image.

Cone Beam Computed Tomography (CBCT) is an imaging technology that has been used in several fields of medicine such as in cardiac imaging, radiotherapy, and in dentistry.

Cone-beam computed tomography or CBCT scanning makes it possible to improve image capture and processing speeds by directing, in contrast to fan-beam computed tomography (conventional CT), a cone-beam source toward an object/subject and obtaining a series of projection images on a flat-panel X-ray detector. In cone-beam computed tomography scanning, a 3-D image is reconstructed from numerous individual scan projections, each taken at a different angle about the subject, whose image data is aligned and processed in order to generate and present data as a collection of volume pixels or voxels.

The processing of CBCT data for obtaining images requires some type of reconstruction algorithm. Various types of image reconstruction have been proposed, generally classified as (i) exact or approximate, or (ii) iterative or analytic. Exact cone-beam reconstruction algorithms, based on theoretical work of a number of researchers, require that the following sufficient condition be satisfied: "on every plane that intersects the imaged object there exists at least one cone-beam source". The widely used Grangeat algorithm, familiar to those skilled in CBCT image processing, is limited to circular scanning trajectory and spherical objects. Only recently, with generalization of the Grangeat formula, is exact reconstruction possible in spiral/helical trajectory with longitudinally truncated data.

In medical applications, CBCT may be used, such as for cardiac imaging, in multiplanar soft tissue imaging, enhanced pretreatment target lesion road-mapping and guidance, and the ability for immediate multi-planar post-treatment assessment. Use of CBCT may translate to a reduction in the use of iodinated contrast media, a decrease in the radiation dose to a patient and an operator, and an increase in the therapeutic index of the patient. In external beam radiation treatment, CBCT is a main imaging modality used for image-guided radiation treatment (IGRT). The CBCT is performed immediately before the radiation treatment to confirm and validate the patient and radiotherapy target position.

CBCT results in a cone-shaped x-ray bundle, with the x-ray source and planar detector (Image Intensifier or in modern days a digital, electronic Flat Panel Detector) rotating around a point (or field) of interest of an object (or alternatively, a patient). The conical shape of the beam distinguishes this technique from helical, conventional CT, which used a fan-shaped beam. As a result of the acquisition of two-dimensional projections throughout this rotation, only one rotation or less is needed to acquire a full three-dimensional dataset. The images received by the detector are then compiled by a computer into volumetric data (primary reconstruction). The image can be visualized as two-dimensional multi-planar reformatted slices or in three dimensions by using surface reconstruction or volume rendering.

The use of CBCT has steadily increased, and the market for CBCT systems has been growing. However, there are some drawbacks that result from data collection methodologies. One drawback is that high-level scattered x-ray radiation generated by the irradiated volume is also received by the planar x-ray image receptor that significantly impairs image quality by creating image reconstruction artifacts and substantially increasing noise. Currently available methodologies to address these image quality problems tend to be expensive and time consuming (in computational time due to the very large 3D data sets). Accordingly, there is a need in the art to address the image quality problems associated with CBCT due to the large amount of x-ray scatter formed by use of a cone beam of x rays.

BRIEF DESCRIPTION OF THE DRAWINGS

FIG. 1 shows the difference between implementation of the KN point exact model on a point-by-point basis (FIG. 1A) and the pencil beam approach that uses a line source of scatter (FIG. 1B).

SUMMARY OF THE INVENTION

In an embodiment, the present invention relates to an imaging system and associated methods, wherein the system comprises: an electromagnetic radiation (x-ray is typical and is used in this particular application) source for directing at beam at an object to be imaged; optionally a modulator placed between the radiation source and the object to be imaged; and a computer for performing image reconstruction calculations based on a desired distribution of image quality. In a variation, cone beam computed tomography (or CBCT) is used as a medical imaging technique.

In one embodiment, the present invention is able to reduce the number of calculations relative to the KN point model by employing "pencil beams" that reduce the number of calculations from $N^3 \times M^2$ calculations using the KN point model approach to $N^2 \times M^2$ calculations using the pencil beam approach. In the pencil beam approach, each pencil beam is treated as an integrated scattering target.

In an embodiment, the present invention relates to an imaging, system and associated methods configured to construct a Computed Tomography (CT) image of the external and internal structure of an object based on ionizing radiation (such as primary x-ray ionizing radiation), wherein the imaging system is configured to apply an analytical model for fast and accurate estimation for the first-order Compton scatter, which is a dominant scatter source for kV x-ray energies. In one embodiment, the Klein-Nishina (KN) formula is used as the analytic differential scattering cross-section. In an embodiment, the modeling for the scatter detected on detector (such as a flat panel detector) is separated into stages. In one variation, a two or more stage separation may be used wherein the stages comprise a dimensional reduction stage to reduce the 3D formulation into 2D by integrating the KN formula along an interaction line (pencil-beam) and a mean attenuation stage to simplify a calculation for attenuation of scatter from each segment of a beam by using an average attenuation path length. In an embodiment, this dimensional reduction to reduce 3D formulation into a 2D formulation using a pencil beam is mathematically expressed as a quartic equation having terms with powers of 4.

DETAILED DESCRIPTION OF THE INVENTION

In one embodiment, the present invention relates to methods and associated instruments/computers using cone beam CT imaging, to do efficient (e.g., fast and accurate) calculations using various new algorithms to produce images that are of good or excellent quality.

In cone-beam computed tomography (CBCT), high-level scattered radiation originating in the irradiated volume significantly impairs image quality by creating image reconstruction artifacts and substantially increasing noise. Thus, in one embodiment of the present invention, scatter correction is performed in CBCT image reconstruction. Thus, the present invention should have clinical relevance to diagnostic imaging and image-guided radiation treatment. In one variation, the present invention relates to correcting the main components of scatter correction using algorithms that consist of an estimation model and a compensation approach.

In an embodiment, the present invention relates to an imaging system and associated methods, wherein the system comprises: an electromagnetic, radiation (x-ray is typical) source for directing a beam at an object to be imaged; optionally a modulator placed between the radiation source and the object to be imaged; and a computer for performing calculations based on a desired distribution of image quality. In a variation, cone beam computed tomography or CBCT) is used as a medical imaging technique.

In one embodiment, the present invention relates to an analytical model for fast and accurate scatter estimation in kV cone-beam CT images.

In one embodiment, the present invention relates to using the Klein-Nishina (KN) formula for Compton scattering, differential cross-section. In one variation, the point scatter along an interaction line of tissue-equivalent medium is integrated to obtain a beam scatter kernel (BSK).

In one embodiment, the present invention relates to using a small imaging field and an in-field scatter calculation. In one variation, the Taylor series of the integrand of the line integral can be approximated by terms up to the $4^{th}$ order, called a "quartic" equation. The integral can also be simplified to an analytical form.

In one embodiment, the attenuation can be calculated in the medium for scattered photons, by assuming that all the scattered photons from a BSK originate from the beam's effective center, weighted by the amount of scatter from each segment of the.

In one embodiment, robust calculations can be performed using, the point scatter theorem for a cubic water phantom ($10\times10\times10$ cm$^3$). In a variation, the results are treated as accurate expectations for comparison.

Figure 1A:
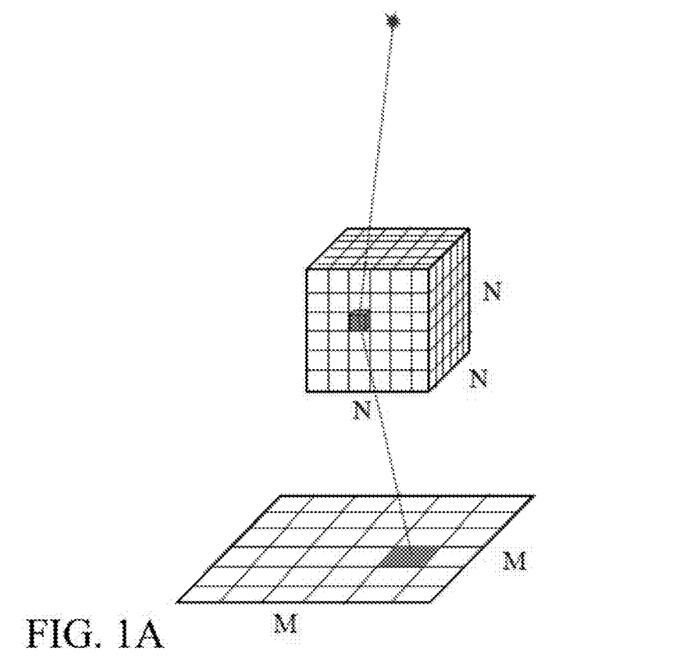
Figure 1B:
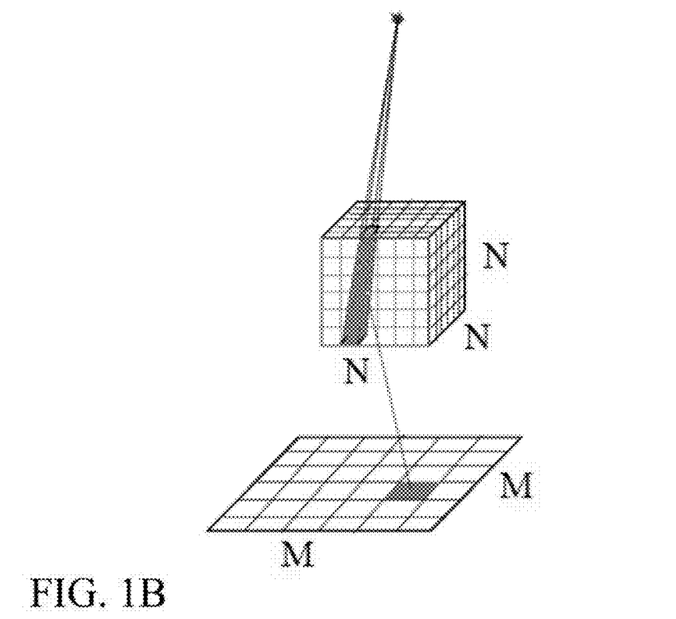

In one embodiment, the present invention is able to reduce the number of calculations relative to the KN point model by employing "pencil beams" that reduce the number of calculations from $N^3 \times M^2$ calculations using the KN point model approach to $N^2 \times M^2$ calculations using the pencil beam approach. In the pencil beam approach, each pencil beam is treated as an integrated target. See FIG. 1, which shows the algorithm geometric difference between the KN point model (FIG. 1A) and the pencil beam approach (FIG. 1B).

In one approximation, the pencil beam approach calculations use the fluence of the incident photon, the differential cross section (using the KN formula) and the linear electron density. The mathematical formula is given by the differential scatter formula $$dN(x) = \Phi(x) \cdot \frac{d\sigma}{d\Omega}(\theta_x) \cdot \rho \cdot dx \cdot d\Omega_x$$

Integrating the formula (without post-scatter attenuation at point P) gives the below quartic approximation:

$$N_{\vec{d}}(\vec{r}) = \int_{x_-}^{x_+} dN(x)dx \approx \frac{[f_0 - f_2 \cdot \|\vec{u}\|^2 + f_4 \cdot \|\vec{u}\|^4] +}{(\vec{r} \cdot \vec{n}) \cdot [f_0' - f_2' \cdot \|\vec{u}\|^2 + f_4' \cdot \|\vec{u}\|^4]}$$

where $$\vec{u} = \vec{r} - (\vec{r} \cdot \vec{n})\vec{n}$$

Figure 2:
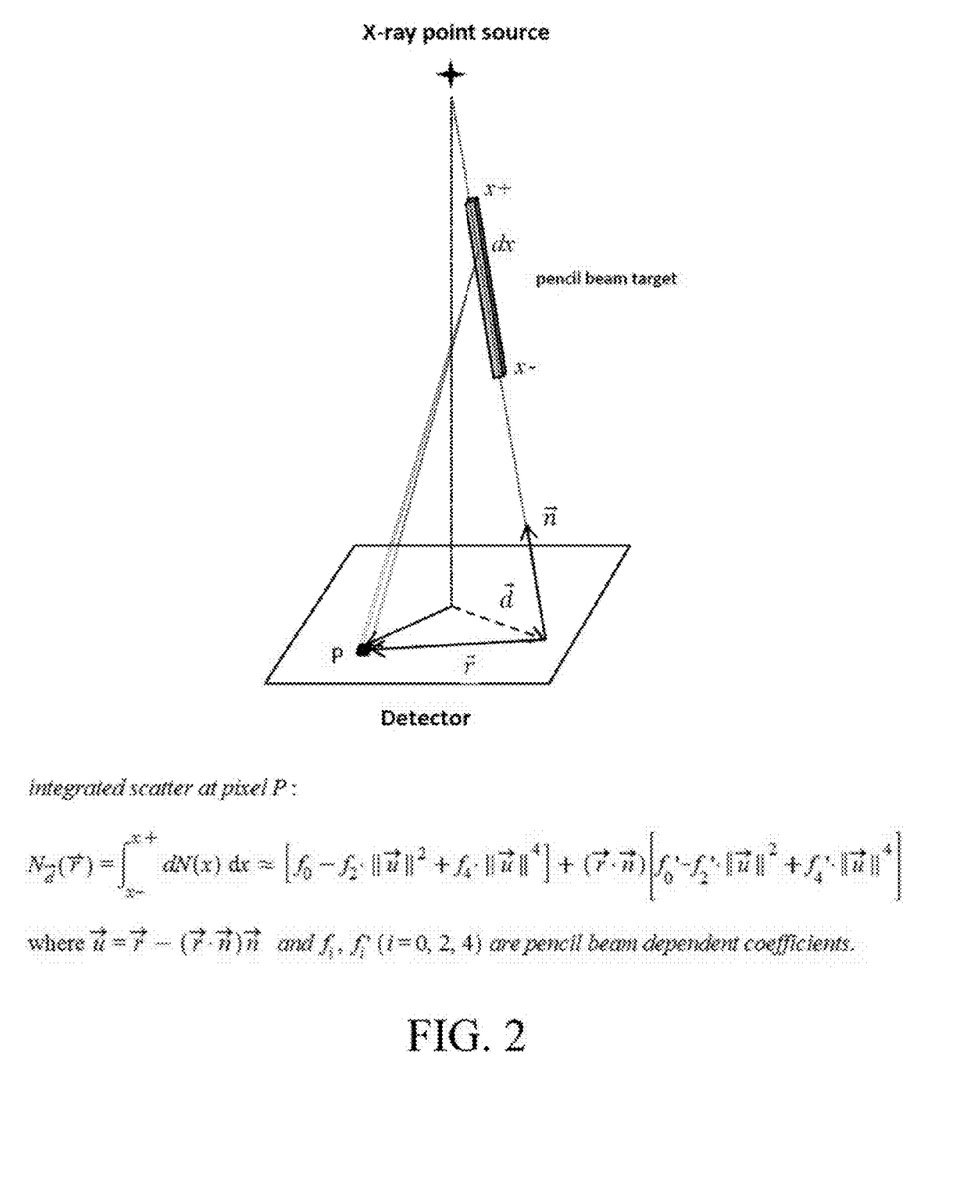
FIG. 2 shows the geometry of FIG. 1B with the various parameters and/or variables that are involved in a calculation using the pencil beam scatter approach.
Figure 3A:
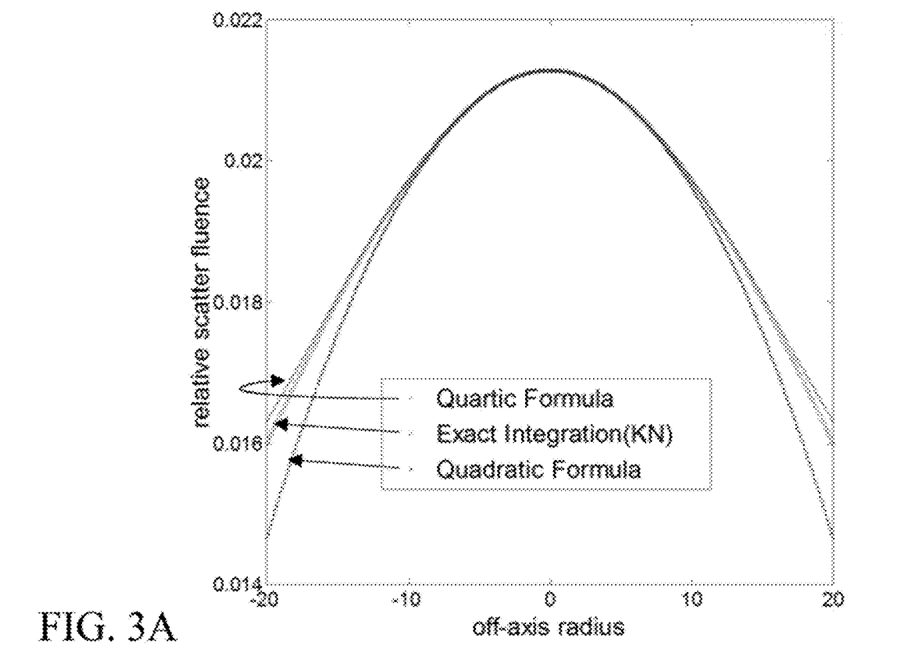
FIGS. 3A and 3B show the integrated scatter at the image receptor plane without post-scatter attenuation for the KN, and quartic pencil beam scatter model (3A), and how the pencil beam approximation can be modeled using an effective "center" of the pencil beam (3B), which also corresponds to FIGS. 1B and 2, wherein the incident primary photons follow exponential attenuation after scattering (post-scatter attenuation) due to interactions in the material being imaged, and relative to a detector pixel, the produced scatter then follows an inverse square law.

The various parameters enumerated above can best be seen in FIG. 2. It is assumed using this approximation that relatively low energy (100 kV) and a relatively small scattering angle are used. FIG. 3A shows the scatter results for the KN exact calculation compared to the quartic pencil beam model without post-scatter attenuation for 100 keV x-rays, a pencil beam length of 20 cm and detector range of 40 cm. A quadratic pencil beam model result is also shown (model only goes to the power of 2, compared to the quartic model that has terms up to a power of 4).

Figure 3B:
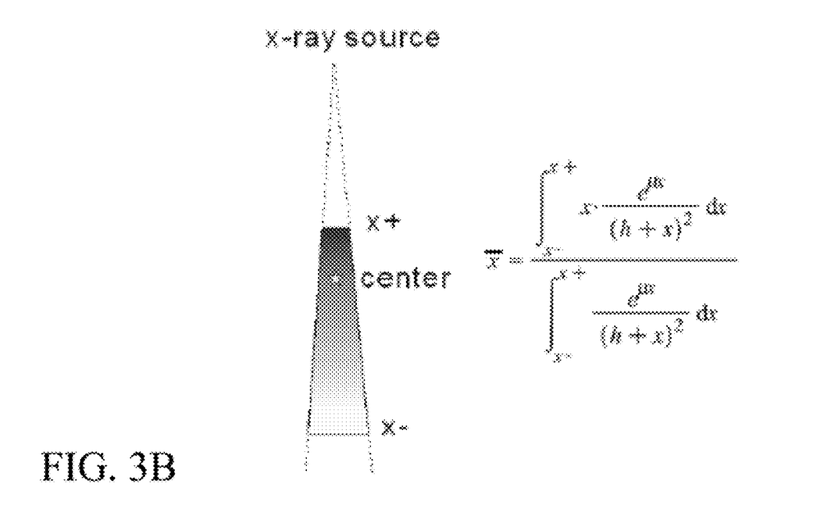

The pencil beam post-scatter attenuation approximation can be modeled using an effective "center" of the pencil beam wherein the incident primary photos follow exponential attenuation, and relative to a detector pixel, the produced scatter follows the inverse square law. See FIG. 3B, FIG. 3B shows the effective "center" of the pencil beam. The post scatter attenuation for the integrated scattered photons follows an exponential attenuation given by:

$$e^{-\mu(E') \cdot l(center, pixel)}$$

The above modeling, not only works on the simplified conditions that include homogenous targets, mono-energetic incident photons and using a free-electron model for Compton scattering, but can also be expanded to heterogeneous targets, poly-energetic incident photons, and binding effects of atomic electrons that are non-trivial for Compton scattering in the low kV energy range. These complex conditions are model in the following manners.

Heterogeneity

For example, the heterogeneity factor $\rho$ is shown in the following formula:

$$dN = (\Phi_0 \cdot e^{-\mu(E) \cdot l}) \cdot \frac{d\sigma}{d\Omega} \cdot \rho \cdot dV \cdot d\Omega$$

The effects include pre-scatter attenuation and electron density. In the above formula, if one assumes that the attenuation coefficient is proportional to electron density (that is the Compton effect is dominant), $\mu(E)$ is taken to be water. The radiological path length 1 can be calculated by the Siddon ray tracing method (described below). Moreover, for integrated scatter, a mean value (i.e., a correction value) for non-uniform electron density is given by the following formula:

$$\overline{\rho} = \frac{l_{rad}}{l_{geo}} = \frac{\int_{x_-}^{x_+} \rho(x)dx}{|x_+ - x_-|}$$

Ray tracing (Siddon's algorithm) describes that a radiological path from point 1 to point 2 can be written as $$d = \sum_i \sum_j \sum_k l(i, j, k)\rho(i, j, k).$$

Figure 4:
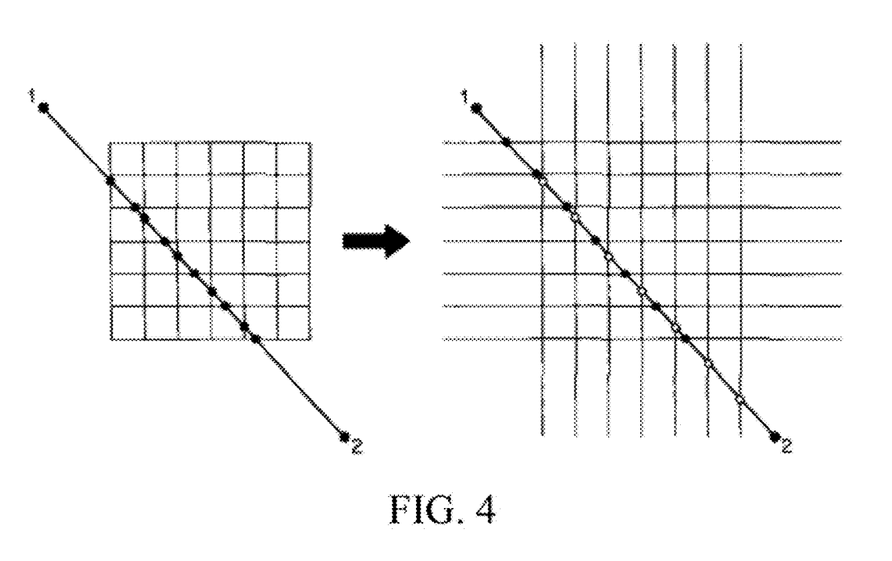
FIG. 4 shows intersections of the ray with the planes are given by three equally spaced sets, depicting the efficient computation algorithm as specified by the Siddon algorithm (Siddon, 1985).

In Siddon's algorithm, voxels are first treated as the intersection volumes of orthogonal sets of parallel planes. The intersections of the ray with the planes are given by three equally spaced sets (see FIG. 4).

Using Siddon's algorithm, a parametric representation of the ray can be shown wherein each interaction may be represented by a parameter $\alpha$, leading to the following formula:

$$X(\alpha) = X_1 + \alpha(X_2 - X_1) \text{ similar for } Y \text{ and } Z$$

The following methodology explains the parametric representation of the ray:

Step 1: Find the maximum and minimum of on the boundaries.

Step 2: Calculate the parameter sets for the intersection of the ray with three sets of orthogonal planes $\{\alpha_x\}$, $\{\alpha_y\}$ and $\{\alpha_z\}$:

Step 3: Merge the parameter sets in ascending order $$\{\alpha\} = \{\alpha_{min}, \text{merge}[\{\alpha_x\}, \{\alpha_y\}, \{\alpha_z\}], \alpha_{max}\} = \{\alpha(0), \ldots, \alpha(n)\}$$

Step 4: Calculate the voxel length $$l(m) = d_{1,2}[\alpha(m) - \alpha(m-1)](m=1, \ldots, n).$$

Step 5: Calculate the indices of the corresponding voxels $\{i(m), j(m), k(m)\}$;

The radiological path now is $$d = \sum_{m=1}^{m=n} l(m)\rho[i(m), j(m), k(m)].$$

In Siddon's method, merging the parameters and calculating the indices of voxels are the two most time consuming steps. The present invention uses an improved Siddon algorithm based on the work of Jacobs (1998) and Han (2000) that uses recursion techniques to find the parameters (no merging is used) and indices (no multiplication is needed). The present methodology employs the following steps:

Step 1: Calculate $\alpha_{min}$ and $\alpha_{max}$ wherein $\alpha = \alpha_{min}$. The initial parameters where the ray first intersects the x, y, and z planes is given by $(\alpha_x, \alpha_y, \alpha_z)$.

Step 2: Calculate the first voxel $(v_x, v_y, v_z)$;

Step 3: Perform recursions;

Update the next parameter $\alpha_\xi = \min(\alpha_x, \alpha_y, \alpha_z)$

Increment the corresponding $\alpha$ along that axis:

Update the next voxel $$v_\xi = \begin{cases} v_\xi + 1, & \text{if } \xi_1 < \xi_2 \\ v_\xi - 1, & \text{if } \xi_1 > \xi_2 \end{cases}.$$

Polyenergetic Photon Spectrum

For example, the terms dependent on photon energy due to a polyenergetic photon spectrum include $e^{-\mu(E)l}$ and the differential $d\sigma/d\Omega$ variable as shown in the following formula:

$$dN = (\Phi_0 \cdot e^{-\mu(E) \cdot \ell}) \cdot \frac{d\sigma}{d\Omega} \cdot \rho \cdot dV \cdot d\Omega$$

Figure 5A:
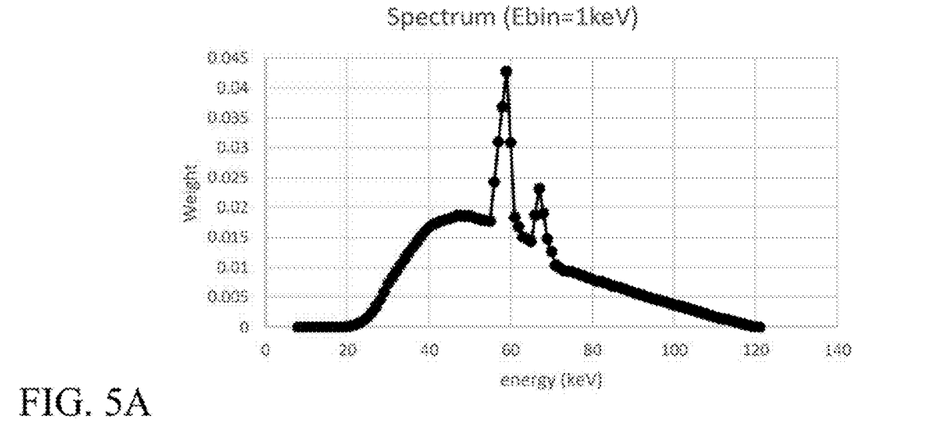
FIGS. 5A and 5B show spectra of poly-energetic incident photons at $E_{bin}=1$ keV and $E_{bin}=5$ keV, respectively derived from a spectrum simulator, for use in testing the analytical pencil beam scatter model.
Figure 5B:
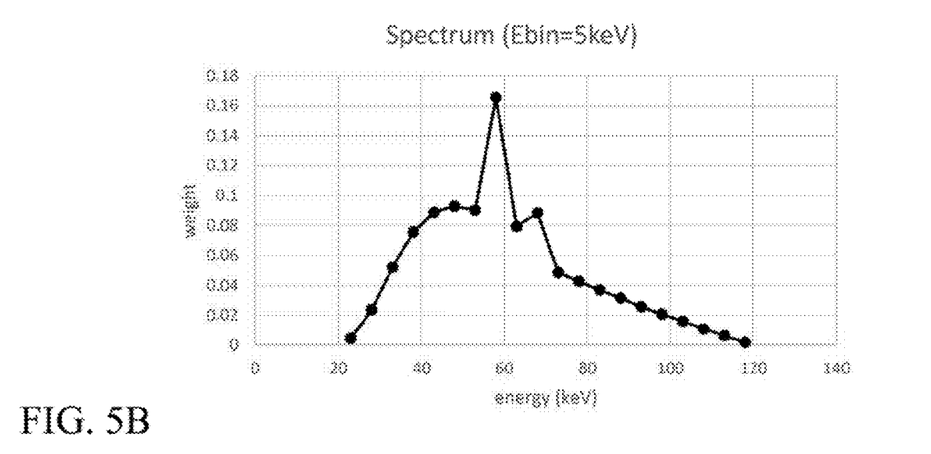

FIGS. 5A and 5B show spectra of 120 kV polyenergetic incident photons with energy bin increments of $E_{bin}=1$ keV and $E_{bin}=5$ keV, respectively, derived from a spectrum simulator far use in pencil beam scattering algorithm testing.

Binding Effect of Atomic Electrons

The binding effect variable $S(E, \theta, Z)$ is shown in the following scattering factor formula:

$$dN = (\Phi_0 \cdot e^{-\mu(E) \cdot \ell}) \cdot \frac{d\sigma}{d\Omega} \cdot \rho \cdot dV \cdot d\Omega \cdot S(E, \theta; Z).$$

Figure 6:
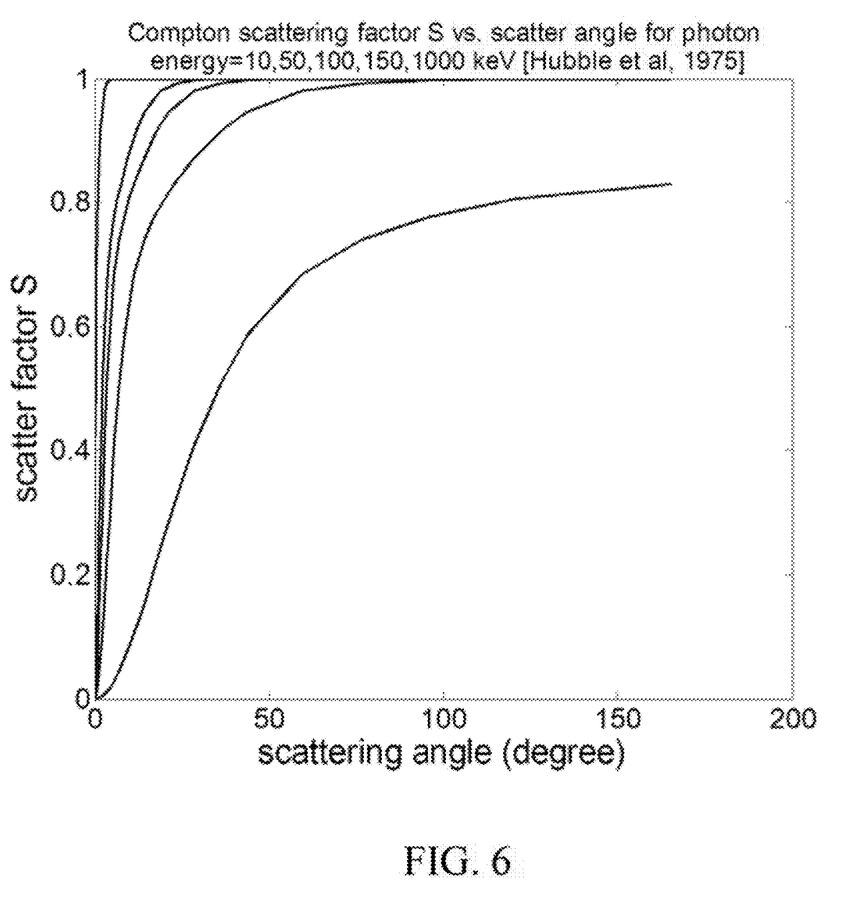
FIG. 6 plots the scattering factor S versus the scattering angle for various photon energies. S varies because Compton scattering angles can be affected by electron binding energy that is non-zero. Values plotted represent biological materials having atomic number≈7.

The scattering factor S vs. the scattering angle for various energies are plotted in FIG. 6. In this plot, the mean value is used showing the scatter angle subtended from the effective center to the pixel. This parameter accounts for changes in scattering angle because of finite electron binding energy, compared to zero binding energy for the free electron that participates in Compton scattering.

Thus, taking into account, the heterogeneity, Polyenergetic photons, and the binding effects of atomic electrons, one derives the following formula:

$$N_{\vec{d}}(\vec{r}) = C \cdot \sum_{E=E_{min}}^{E_{max}} \chi(E) \cdot \underbrace{e^{-\mu(E) \cdot \ell(S,O)}}_{\text{pre-scatter attenuation}} \cdot \overline{\rho}_{water}^{med} \cdot \underbrace{\{f(\vec{r})\}}_{\text{quartic expression}} \cdot \overline{S}(E, \theta_{center}) \cdot \underbrace{e^{-\mu(E) \cdot \vec{\ell}}}_{\text{post-scatter attenuation}}$$

wherein C is a constant and the three unmarked parameters in the above formula are variables that account for the spectrum, serve as a correction for heterogeneity and as a correction for binding effects, respectively. Importantly, the "quartic expression" is the expression previously explained:

$$N_{\vec{d}}(\vec{r}) = \int_{x-}^{x+} dN(x) dx \approx \begin{array}{l} [f_0 - f_2 \cdot \|\vec{u}\|^2 + f_4 \cdot \|\vec{u}\|^4] + \\ (\vec{r} \cdot \vec{n}) \cdot [f_0' - f_2' \cdot \|\vec{u}\|^2 + f_4' \cdot \|\vec{u}\|^4] \end{array}$$

where $$\vec{u} = \vec{r} - (\vec{r} \cdot \vec{n}) \vec{n}$$

Figure 7:
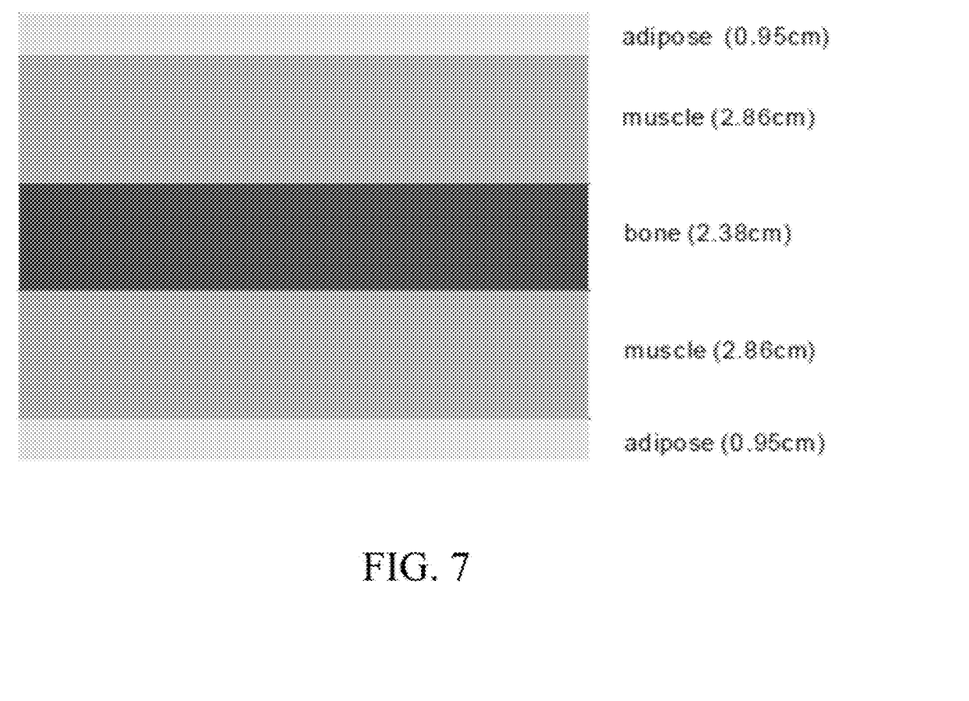
FIG. 7 shows the phantom sample that was used for testing the analytical pencil beam scatter model.
Figure 8:
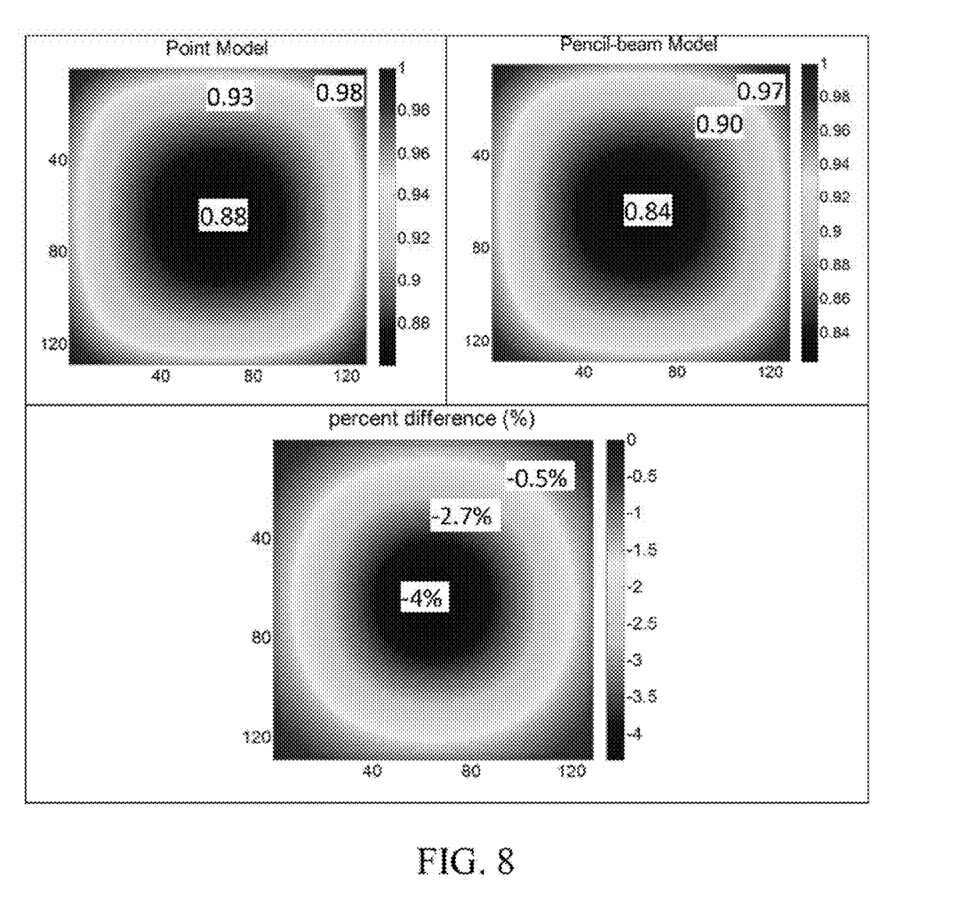
FIG. 8 shows scatter results with 21×21×21 voxels for the KN exact calculation (upper left image), the analytical pencil beam scatter model as the upper right image, and a percent difference map comparison of the KN and pencil beam results as the bottom image.

The above formula with all incorporated terms was validated on a phantom sample (as shown in FIG. 7) wherein E=120 kV, SAD=100 cm, SDD=150 cm, FS=10×10 cm, and the detector size 15×15 cm. The detector contained 128×128 pixels, and the phantom calculations used 21×21×21 voxels and 21×21 pencil-beams. The calculated scatter results are shown in FIG. 8 with the 21×21×21 voxels for the KN exact calculation shown as the upper left image and the analytical pencil beam scatter model shown as the upper right image. The percent difference map that compares the KN and pencil beam scatter results is shown as the bottom image.

Figure 9A:
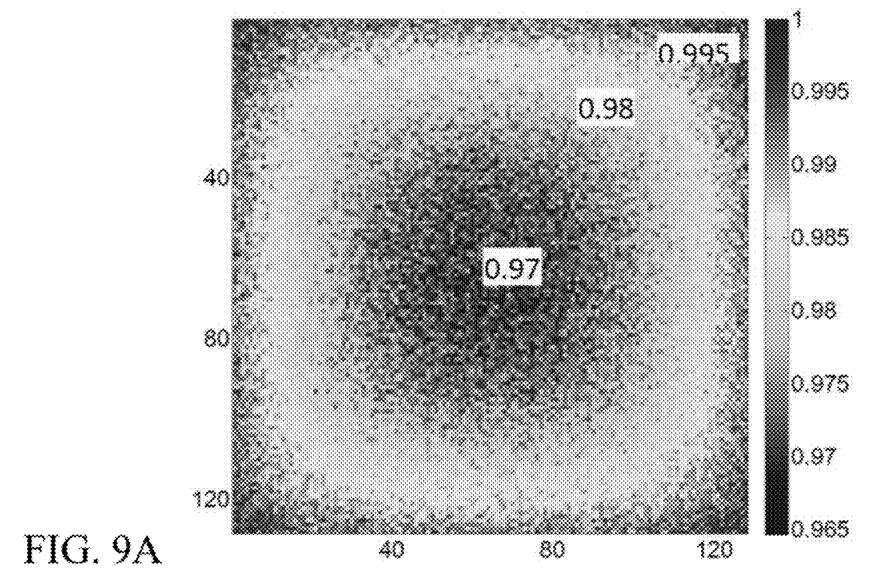
FIG. 9A shows the scatter results for the geometry of FIG. 2 created by Monte Carlo simulations and FIG. 9B shows a profile of the image along the horizontal center line. This Monte Carlo computation does not properly count the amount of Compton scattering reaching the image receptor plane. Monte Carol simulations are used for validation of the analytical pencil beam scatter model.
Figure 9B:
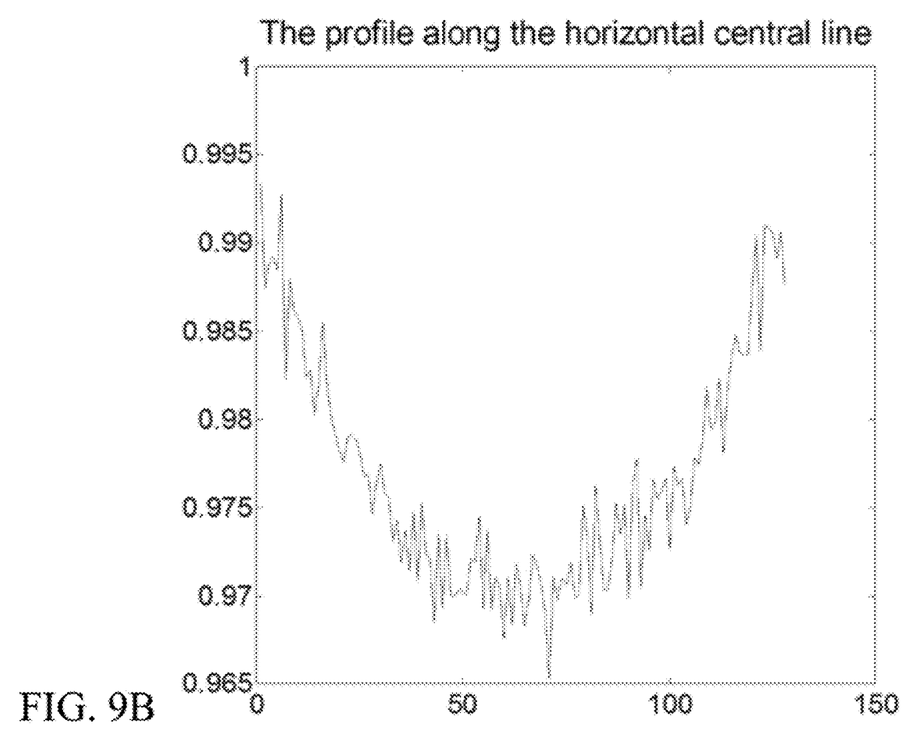

Subsequently Monte Carlo simulations were performed on the same phantom slab geometry (as shown in FIG. 7). FIG. 9A shows the results of an image created by these Monte Carlo simulations and FIG. 9B shows a profile of the image along the horizontal center line. It should be noted that the images from the actual experiments (FIG. 8) were more uniform relative to the image from the Monte Carlo calculations (FIGS. 9A and 9B).

In a Monte Carlo experiment done with a homogenous slab, $10^7$ photons were simulated with the binding effect considered and non-considered. The following Table 1 shows the results:

TABLE 1

|  | Binding Effect On | Binding Effect Off |
|---|---|---|
| Total 1$^{st}$-order Compton photons | 2252170 | 2245581 |
| 1$^{st}$-order Compton photons on detector (in-field area) | 78063 | 31438 |

In the simulation, as $d\sigma/d\Omega|_{bound} = d\sigma/d\Omega|_{KN}(S)$ and S=1, the decreased differential cross section means that there is less possibility of an occurrence (on the detector). It is expected that scatter with the binding effect should be less than that without the binding effect.

The outcome of the bound Compton scattering was not solitary. In the EGSnrc, which was run (compared to the previous version EGS4), the outcome of a bound Compton event may be any of the following:

1. One scattered photon+a Compton electron;
2. One scattered photon+a Compton electron+several relaxation particles (fluorescent x-rays, Auger electrons, Coster-Kronig electrons);
3. The original photon, when interaction is rejected.

In the simulation, all three were marked as Compton events. However, if outcome 3 is not considered (because it may not be considered to be Compton scatter), one can re-run the simulation. The results showing the raw data of this experiment are shown in Table 2 and the images are shown in FIG. 10:

TABLE 2

|  | Binding Effect On | Binding Effect Off |
| --- | --- | --- |
| Total 1$^{st}$-order Compton photons | 2188465 | 2245581 |
| 1$^{st}$-order Compton photons on detector (in-field area) | 20548 | 31438 |

Figure 10A:
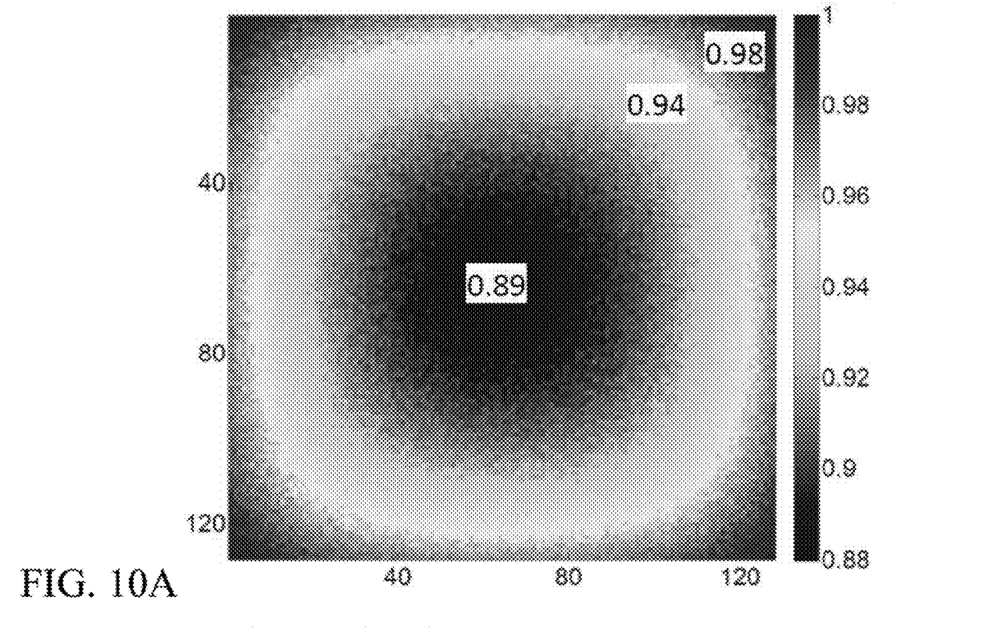
FIG. 10A shows the scatter results for the geometry of FIG. 2 created by Monte Carlo simulations and FIG. 10B shows a profile of the image along the horizontal center line wherein original photon interaction is rejected. This Monte Carlo computation properly counts the amount of Compton scattering reaching the image receptor plane. Monte Carlo simulations are used for validation of the analytical pencil beam scatter model.
Figure 10B:
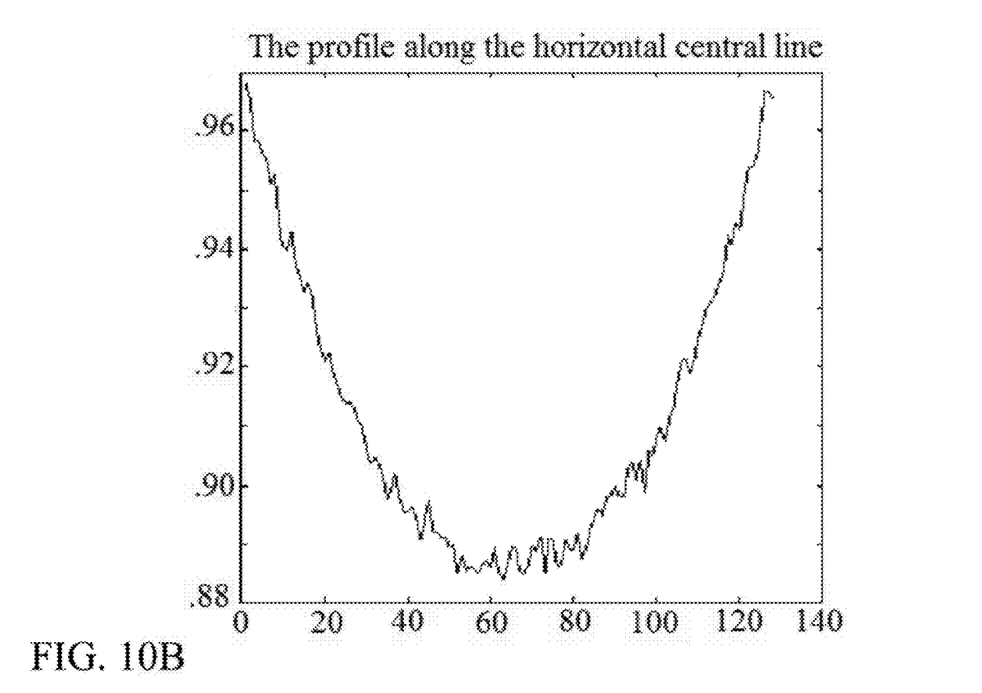

FIG. 10A and FIG. 10B show the image using the Monte Carlo simulation wherein outcome 3 above is not considered and the profile along the horizontal central line, respectively.

The calculations showed a systematic overestimation of about 10% in average for either a perpendicular or a tilted beam on the absolute value of scatter fluence. However, the largest difference on the relative scatter distribution is as low as 0.4% and 2.5% for perpendicular and tilted beams, respectively. The largest relative difference for the whole phantom is about −1.8%. In computation time, the integrated scatter model was faster by over 2 orders than the point kernel (exact KN) method.

Thus, in an embodiment, the present invention relates to algorithms that provide a set of approximations and associated methods that reduce the computational complexity, and the amount of projection data to be processed for tomography. In an embodiment reconstruction computation is simplified, and made faster by reducing the number of image elements that must be computed, thereby simplifying the computation of the intersection of a ray with an image element. As a result, in an embodiment, the present invention relates to an improved method of performing tomography with reduced computational complexity.

In an embodiment, the present invention relates to an analytical scatter model that shows excellent results in the computation of small objects (such as a cubic water phantom). The results were compared to the result attained by the fully integrated point scatter (exact KN) approach. The difference in relative scatter distribution at each detector pixel in the image receptor plane is in the range of −1.8%~+0.3%, which shows that the behavior of scatter distribution is well estimated by the present pencil beam model. Additionally, the integrated scatter model was faster by over 2 orders of magnitude relative to that achieved using the point kernel method, illustrating very high computational efficiency in scatter estimation.

In an embodiment, the present invention relates to a kV scatter model that shows a very high computational efficiency in scatter estimation. In one variation, the expected behavior of scattering distribution is observed and well estimated. In one embodiment, the present invention validates thoroughly for relatively small imaging fields (~10×10 cm$^2$) and the model will likely be useful and have great potential in the cases of imaging small objects and interior reconstruction.

In an embodiment, the present invention relates to a cone-beam computed tomography instrument that comprises a computer and software, wherein the software contains computer executable instructions that allows a user to generate a digital radiographic 3D volume image reconstruction of an object, executed at least in part on the computer, comprising: obtaining image data for a plurality of 2D projection images over a range of scan angles: generating, for each of the plurality of 2D projection images a spatial resolution projection image by: allowing the computer to access the software, wherein said software comprises an algorithm that reduces the number of calculations from N$^3$×M$^2$ calculations to N$^2$×M$^2$ calculations.

In a variation, the computer accesses software comprising an algorithm that corrects scatter for one or more of heterogeneity in the object, poly-energetic incident photons, and binding effects of atomic electrons. In a variation, the computer accesses software comprising an algorithm that corrects scatter for at least two of heterogeneity in the object, poly-energetic incident photons, and binding effects of atomic electrons. In another variation, the computer accesses software comprising an algorithm that corrects scatter for all of heterogeneity in the object, poly-energetic incident photons, and binding effects of atomic electrons.

In one embodiment, the cone-beam computed tomography instrument may use software that has computer executable instructions that use a pencil beam scatter model approach. In one variation, use of the algorithm was faster by over 2 orders of magnitude relative to that achieved using a point kernel method.

In an embodiment the present invention relates to a method for digital radiographic 3D volume image reconstruction of an object, executed at least in part on a computer, comprising computer executable instructions that allows a user to generate a digital radiographic 3D volume image reconstruction of an object, executed at least in part on the computer, comprising: obtaining image data for a plurality of 2D projection images over a range of scan angles; generating, for each of the plurality of 2D projection images a spatial resolution projection image by: allowing the computer to access the software, wherein said software comprises an algorithm that reduces the number of calculations from N$^3$×M$^2$ calculations to N$^2$×M$^2$ calculations.

In one variation, the method uses an algorithm further corrects for one or more of heterogeneity in the object, poly-energetic incident photons, and binding effects of atomic electrons. In a variation, the algorithm may correct for at least two of heterogeneity in the object, poly-energetic incident photons, and binding effects of atomic electrons. In a variation, the algorithm may correct for all of heterogeneity in the object, poly-energetic incident photons, and binding effects of atomic electrons. In one variation, the method's use of the algorithm was faster by over 2 orders of magnitude relative to that achieved using a point kernel method.

In an embodiment, the present invention relates to a computed tomography imaging system configured to construct an image of an object, the imaging system comprising: a radiation source; a detector configured to detect the radiation; and at least one processing circuit configured to generate the image and/or access software, wherein said software comprises an algorithm that reduces the number of calculations from N$^3$×M$^2$ calculations to N$^2$×M$^2$ calculations.

In a variation, the computed tomography imaging system may use an algorithm that corrects for one or more of heterogeneity in the object, poly-energetic incident photons, and binding effects of atomic electrons. In one variation, the computed tomography imaging system uses an algorithm that corrects for two or more of heterogeneity in the object, poly-energetic incident photons, and binding effects of atomic electrons. In a variation, the algorithm corrects for all of heterogeneity in the object, poly-energetic incident photons, and binding effects of atomic electrons.

In an embodiment, the computed tomography imaging system having at least one processing circuit that is configured to generate the image produces an image wherein relative scatter distribution at, each detector pixel in an image receptor plane is in a range of −1.8%~+0.3% relative to using a fully integrated point scatter approach.

In one variation, the computed tomography imaging system uses an algorithm that is faster by over 2 orders of magnitude relative to that achieved using a point kernel method.

It should be understood that although CBCT has been used principally in the medical field there are other technologies where the system and associated methodologies may be useful, such as in security related applications and non-destructive testing.

In an embodiment, the 2D integrated, scatter model showed high computational efficiency in scatter estimation.

It should be understood that it is contemplated and therefore within the scope of the invention that any of the above described features may be combined with any other feature even if they are not described together. Minor modifications to the instrument, systems, and methods of the present invention are contemplated and therefore within the scope of the invention. Nevertheless, the invention is described by the below claims.

We claim:

1. A cone-beam computed tomography instrument that comprises a non-transitory computer readable recording medium encoded with a computer program, which when executed by a computer system causes the computer system to execute a digital radiographic 3D volume image reconstruction of an object, executed at least in part on the computer system, comprising: obtaining image data for a plurality of 2D projection images over a range of scan angles; generating, for each of the plurality of 2D projection images a spatial resolution projection image by: allowing the computer system to access the computer program, wherein said computer program comprises an algorithm that reduces the number of calculations from $N^3 \times M^2$ calculations to $N^2 \times M^2$ calculations, wherein the computer system accesses the computer program comprising an algorithm that corrects scatter for one or more of heterogeneity in an object being imaged, poly-energetic incident photons, and binding effects of atomic electrons.

2. The cone-beam computed tomography instrument of claim 1, wherein the computer system accesses the computer program comprising an algorithm that corrects scatter for at least two of heterogeneity in the object, poly-energetic incident photons, and binding effects of atomic electrons.

3. The cone-beam computed tomography instrument of claim 1, wherein the computer system accesses the computer program comprising an algorithm that corrects scatter for all of heterogeneity in the object, poly-energetic incident photons, and binding effects of atomic electrons.

4. The cone-beam computed tomography instrument of claim 1, wherein said computer program has computer executable instructions that use a pencil beam scatter model approach.

5. The cone-beam computed tomography instrument of claim 1, wherein use of the computer program was faster by over 2 orders of magnitude relative to that achieved using a point kernel method.

6. A method for digital radiographic 3D volume image reconstruction of an object on a non-transitory computer readable recording medium encoded with a computer program, which when executed by a computer system causes the computer system to execute a digital radiographic 3D volume image reconstruction of an object, wherein said method comprises: obtaining image data for a plurality of 2D projection images over a range of scan angles; generating, for each of the plurality of 2D projection images a spatial resolution projection image by: allowing the computer system to access the computer program, wherein said computer program comprises an algorithm that reduces the number of calculations from $N^3 \times M^2$ calculations to $N^2 \times M^2$ calculations and wherein the computer program comprises an algorithm that corrects scatter for one or more of heterogeneity in an object being imaged, poly-energetic incident photons, and binding effects of atomic electrons.

7. The method of claim 6, wherein said computer program comprises an algorithm that corrects scatter for at least two of heterogeneity in the object, poly-energetic incident photons, and binding effects of atomic electrons.

8. The method of claim 6, wherein said computer program comprises an algorithm that corrects scatter for all of heterogeneity in the object, poly-energetic incident photons, and binding effects of atomic electrons.

9. The method of claim 6, wherein use of the computer program was faster by over 2 orders of magnitude relative to that achieved using a point kernel method.

10. A computed tomography imaging system configured to construct an image of an object, the imaging system comprising: an x-ray radiation source; a detector configured to detect the x-ray radiation; and at least one non-transitory computer readable recording medium encoded with a computer program, which when executed by a computer system causes the computer system to generate the image and/or access the computer program, wherein said computer program comprises an algorithm that reduces the number of calculations from $N^3 \times M^2$ calculations to $N^2 \times M^2$ calculations, wherein the algorithm corrects scatter for one or more of heterogeneity in an object being imaged, poly-energetic incident photons, and binding effects of atomic electrons.

11. The computed tomography imaging system of claim 10, wherein the computer program corrects scatter for two or more of heterogeneity in the object, poly-energetic incident photons, and binding effects of atomic electrons.

12. The computed tomography imaging system of claim 10, wherein the computer program corrects scatter for all of heterogeneity in the object, poly-energetic incident photons, and binding effects of atomic electrons.

13. The computed tomography imaging system of claim 10, wherein the computer program is configured to generate an image, wherein relative scatter distribution at each detector pixel in an image receptor plane is in a range of −1.8%~+0.3% relative to using a fully integrated point scatter approach.

14. The computed tomography imaging system of claim 11, wherein use of the computer program was faster by over 2 orders of magnitude relative to that achieved using a point kernel method.

15. The computed tomography imaging system of claim 13, wherein use of the computer program was faster by over 2 orders of magnitude relative to that achieved using a point kernel method.

* * * * *